United States Patent [19]

Widlund et al.

[11] Patent Number: 4,564,108

[45] Date of Patent: Jan. 14, 1986

[54] PACKAGE FOR SANITARY NAPKINS

[75] Inventors: Leif U. R. Widlund; Stefan Nedestam, both of Mölnlycke; Arne Fröidh, Stenungsund, all of Sweden

[73] Assignee: Molnlycke AB, Gothenburg, Sweden

[21] Appl. No.: 620,076

[22] Filed: Jun. 12, 1984

[30] Foreign Application Priority Data

Jun. 14, 1983 [SE] Sweden ................................ 8303383

[51] Int. Cl.4 ............................................ A61F 13/16
[52] U.S. Cl. .................................... 206/438; 206/494; 206/820
[58] Field of Search ............... 206/438, 440, 441, 494, 206/495, 820; 604/387, 389

[56] References Cited

U.S. PATENT DOCUMENTS

| 1,386,398 | 8/1921 | Davis | 206/820 |
|---|---|---|---|
| 2,140,748 | 12/1938 | Johanson | 206/800 |
| 2,210,196 | 8/1940 | Baldwin | 206/800 |
| 3,035,578 | 5/1962 | Elmore | 206/438 |
| 3,070,102 | 12/1962 | MacDonald | 206/820 |
| 3,921,802 | 11/1975 | Thompson | 206/820 |
| 4,182,336 | 1/1980 | Black | 206/438 |
| 4,298,158 | 11/1981 | Hoppe et al. | 206/820 |
| 4,458,814 | 7/1984 | Meschi | 206/820 |

FOREIGN PATENT DOCUMENTS

| 962805 | 2/1975 | Canada | 604/389 |
|---|---|---|---|
| 1274794 | 10/1963 | Fed. Rep. of Germany | 206/441 |
| 1904070 | 1/1969 | Fed. Rep. of Germany | 206/820 |
| 1376625 | 9/1964 | France | 206/820 |
| 559760 | 9/1911 | Switzerland | 206/440 |
| 600443 | 4/1948 | United Kingdom . | |
| 671148 | 4/1952 | United Kingdom . | |
| 878252 | 9/1961 | United Kingdom . | |
| 962752 | 7/1964 | United Kingdom . | |
| 1323319 | 7/1973 | United Kingdom . | |
| 1401991 | 8/1975 | United Kingdom . | |
| 2081102 | 2/1982 | United Kingdom | 604/387 |

Primary Examiner—William T. Dixson, Jr.
Assistant Examiner—Brenda J. Ehrhardt
Attorney, Agent, or Firm—Young & Thompson

[57] ABSTRACT

A package for menstrual protectors such as sanitary napkins and pads or panty protectors has one side coated with pressure-sensitive adhesive for securing the napkin to the underwear of the user. A plurality of napkins have their adhering side releasably fixed to a plastic film or the like. When the film with the attached napkins is folded, the napkins are placed on top of each other forming one or more piles enclosed by the film. The overlapping edges of the film extending laterally beyond the protectors are then sealed together.

19 Claims, 12 Drawing Figures

PACKAGE FOR SANITARY NAPKINS

The present invention relates to a package for menstrual protectors such as sanitary napkins and pads or panty protectors which have, on the side facing away from the wearer when in use, areas coated with a pressure sensitive adhesive intended for sticking to the underwear of the user to keep the sanitary napkin in place.

The altogether predominant type of attachment means used today for sanitary napkins and panty protectors consists of such adhesive areas applied on the backsides thereof. This method of fastening sanitary napkins seems to be the simplest conceivable, which functions very well.

Sanitary napkins known up to now with fastening means in the form of adhesive also have certain disadvantages however; the napkins must be made so as to cover the adhesive applied on their backsides before being used in order to prevent unintentional sticking together of the napkins in a package. So far, this drawback has been overcome by applying a protective paper coated with a release agent such as silicone across the adhesive areas.

Silicone-coated paper, so-called release paper, is however expensive thus constituting a substantial part of the material costs of the sanitary napkin. With regard to low-price products in particular, the cost of the release paper would be quite unacceptable in relation to the total material cost.

So far, the packing of a number of sanitary napkins provided with release paper into a multi-piece package such as a carton or a bag has been a complicated and timeconsuming process as it has proved difficult to pack the napkins mechanically while keeping up with the rate of production in the manufacturing plant.

With the present invention, these disadvantages have been eliminated.

According to the invention, a package for sanitary napkins of the kind mentioned by way of introduction is characterized in that a plurality of sanitary napkins are detachably applied with mutual spacing in one or more rows with their adhesive side facing a film preferably of paper or plastics, the film with the napkins placed thereon being folded and/or rolled up so that the napkins will lie on top of one another in one or more piles, the film also enclosing in its folded and/or rolled-up condition the sanitary napkins disposed thereon.

In this way, the use of a separate release paper on each individual napkin has been eliminated. The function of the release paper is taken over by the film, which furthermore serves as packing material. By virtue of the fact that the sanitary napkins to be included in a package are joined together on the flim already, the packaging process is simplified as compared with previous methods involving the above-mentioned problems in handling a number of separate sanitary napkins for mechanical packing.

The invention will be described in more detail while referring to a number of exemplary embodiments shown in the accompanying drawings, of which FIG. 1 is a plan view and FIG. 2 a cross section of the type of sanitary napkins intended for packing.

FIG. 3 illustrates a number of sanitary napkins of the kind indicated in FIGS. 1 and 2 while placed on a package blank for a first embodiment of the invention, whereas

FIG. 7 illustrates a number of sanitary napkins disposed on a package blank for a second embodiment of the package according to the invention, whereas

Figure 1:
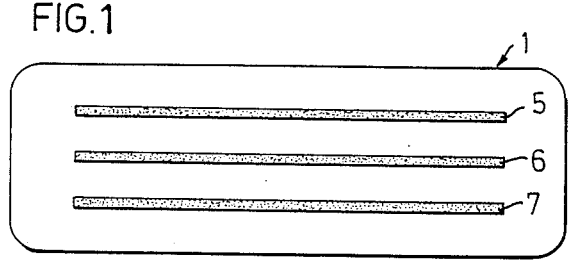
Figure 2:
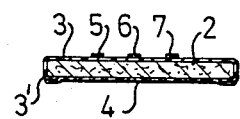

FIGS. 1 and 2 show a menstrual protector in the form of a thin napkin 1 which consists of a compressed core 2 of cellulose mass. One side of the absorption core is coated with a liquid-impermeable layer 3, suitably of polyethylene, this layer with portions 3' being folded around the side edges of the core 2 and a short distance further in over the opposite side surface of the core. The layer 3 is joined there to a layer 4 which, when using the napkin, is in contact with the body of the user and which consists of a liquid-permeable layer, preferably non-woven textile. A number of adhesive strips 5, 6 and 7 are applied on the outside of the liquid-impermeable layer 3, which strips suitably consist of hot-melt glue and are intended for adhesion to the underwear of the user to keep the napkin or pad in place during use.

Figure 3:
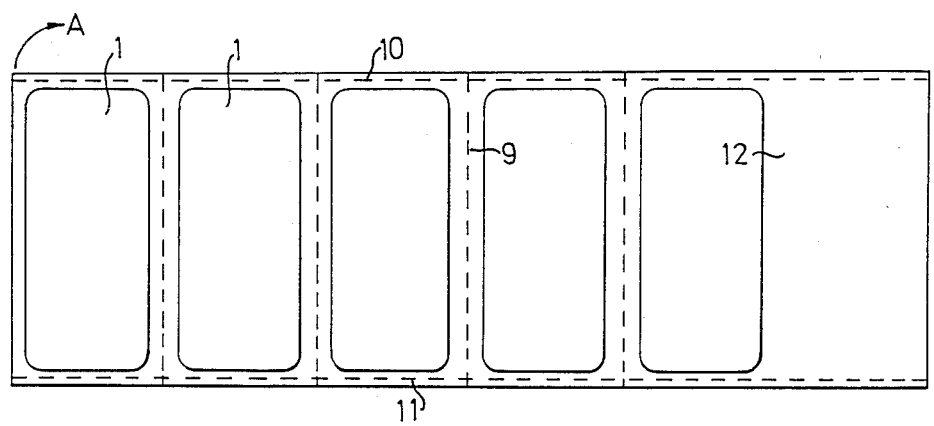

In the embodiment illustrated in FIG. 3 for a package according to the invention, a number of napkins 1 of the kind indicated in FIGS. 1 and 2 are placed with their adhesive surface in contact with a plastic film 8. The napkins 1 are mutually spaced, and in the gap between the adjoining napkins the film is provided with perforations 9. The side of the plastic film 8 which is intended as contact surface for the napkins is treated with a release agent such as silicone, or is embossed for reducing the adhesive effect between the film and the napkins. As a result of the perforations 9, indidvidual napkins as well as a protective film layer, formed by the plastic film 8 and applied across the adhesive strips on each of the napkins, can be removed from the package. The plastics film 8 also has longitudinal perforations 10,11 situated outside the end edges of the napkins and intended, as is more closely described below, to facilitate the opening-up of the package.

Figure 4:
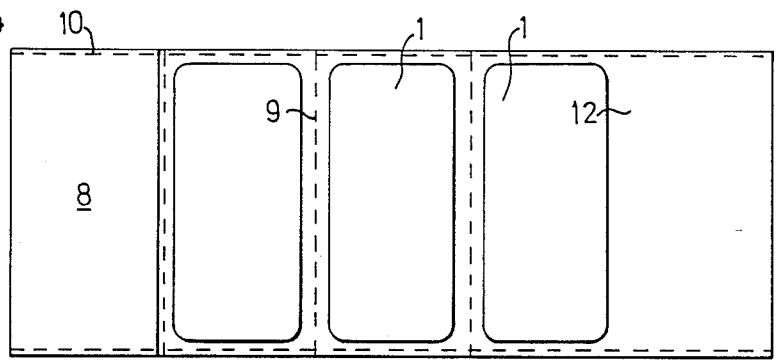
FIG. 4 illustrates the unit shown in FIG. 3 during its stage of folding together into a package.
Figure 5:
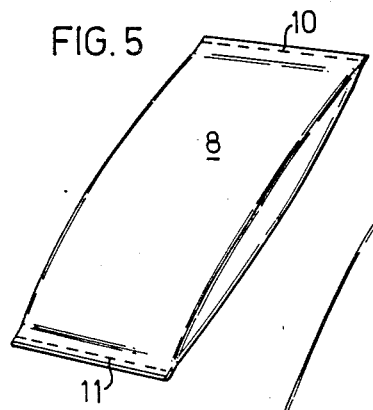
FIG. 5 illustrates the finished package and FIG. 6 the way of opening the package for releasing a sanitary napkin.

As will be seen from FIG. 4, the package blank 8 with napkins 1 placed thereon is rolled up according to the arrow A shown in FIG. 3. After the film 8 with the attached napkins has been rolled up so that the napkins are piled up on top of one another, the side edges of the film are welded together outside the perforations 10,11 thus forming the entirely sealed package according to FIG. 5. As shown in FIGS. 3 and 4, the plastic film 8 has an end portion 12 on which no napkin is placed. This portion is located farthest out in the finished package, serving as a protective flap.

Figure 6:
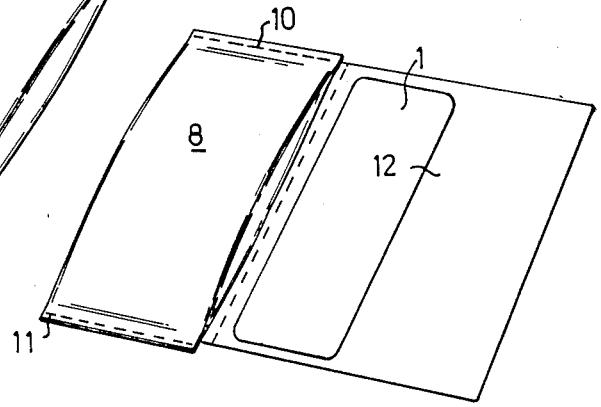

The package is opened by tearing off along the perforations 10,11 thus uncovering the napkins 1 one by one, as shown in FIG. 6.

Figure 7:
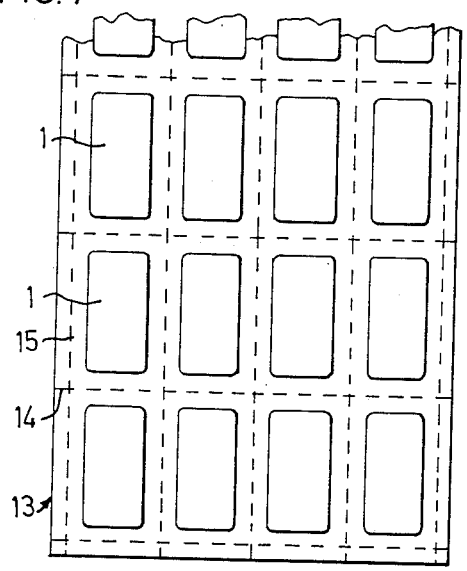

FIG. 7 illustrates a package according to a second embodiment of the invention in its spread-out condition. The sanitary napkins 1 have been placed here in several rows on the plastic film 13 which is provided with transverse as well as longitudinal perforations 14,15 delimiting one plastic film portion for each individual sanitary napkin.

Figure 8:
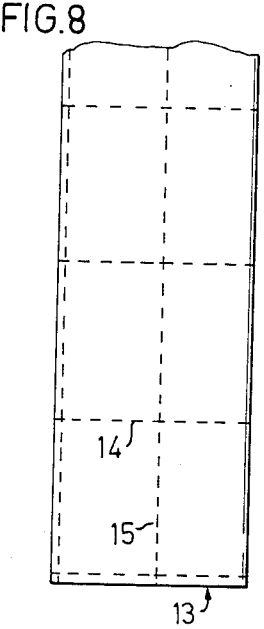
FIG. 8 illustrates a step in the process of forming a package from the blank shown in FIG. 7.

FIG. 8 illustrates the way of first folding the package blank 13, whereafter the unit obtained can be rolled or folded together into a pile for example, with two napkins 1 placed side by side. Such a package may for example contain 20 napkins. A package of this size is not very bulky but can easily be carried in a handbag. Sealing of the package can be done by welding or gluing, preferably by means of hot melt.

Figure 9:
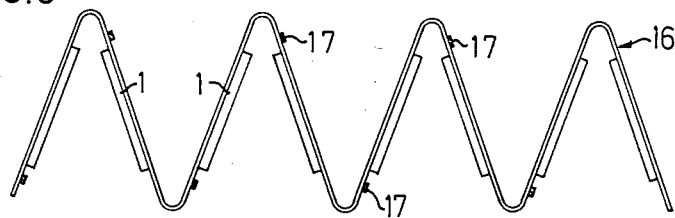
FIG. 9 illustrates schematically the process of forming a package according to a third embodiment.

In the embodiment of the package illustrated in FIG. 9, a number of sanitary napkins 1 have also been applied with their adhesive side facing one side of a plastic film 16 which has been embossed or treated with release agent. In this case, however, the package unit has not been rolled but instead folded in zigzag, as shown in the figure. The folded-up package unit is kept together with the aid of hot melt spots applied to the plastic film 17. The plastic film 16 is suitably perforated between the individual sanitary napkins.

Figure 10:
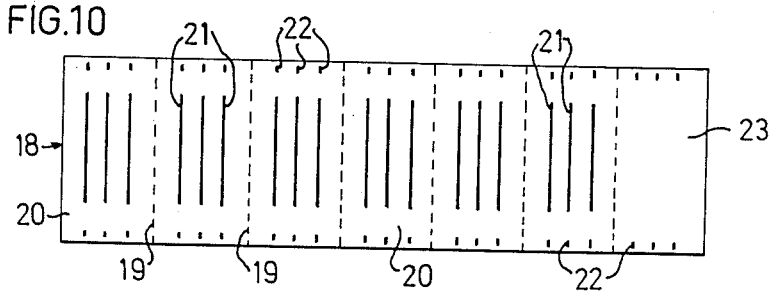
FIG. 10 illustrates a package blank similar to that shown in FIG. 3, while FIGS. 11 and 12 finally illustrate a fourth and a fifth embodiment of the package according to the invention.

A suitable method of manufacturing and packing sanitary napkins or pads is schematically illustrated in FIG. 10. Sanitary napkins (not shown here) are manufactured with an absorbent cellulose core surrounded on one side by a first layer of a liquid-impermeable material such as polyethylene, and on the opposite side by a second non-woven textile layer. In contrast to the case with the napkin shown in FIG. 1, the adhesive strips are applied only in connection with packing the napkins. FIG. 10 shows an elongate plastic film 18 having five areas 20 for the same number of sanitary napkins, which areas are delimited by means of perforations 20. The side of the plastic film to which the napkins are to be applied can be provided with a release agent such as silicone, or it can be embossed. Within each area on this side, the film is also provided with three central hot melt strips 21 and three hot melt spots 22 at either end of the respective area. With their plastic layer side, the sanitary napkins are to be fixed to the central hot melt strings which, upon removal of each individual napkin from the plastic package film, are transferred from there and onto the respective napkin. The hot melt spots 22 are intended for sealing the package unit when this unit is subsequently rolled together. Due to the release agent treatment or embossment of the plastic film 18, the package unit is easily openable and reclosable. The plastic film 18 as well has an extending portion 23 serving as a protective flap at the outermost end of the package.

Figure 11:
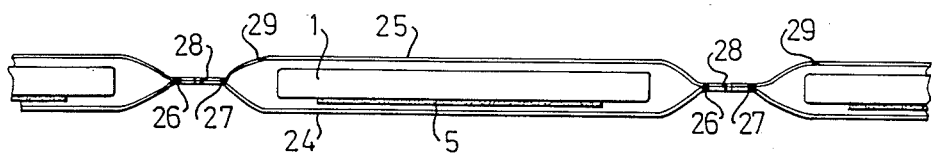

FIG. 11 illustrates a somewhat modified package according to the invention. Included therein are two plastic films; a first film 24 having one side treated with release agent onto which the adhesive side of the sanitary napkin is applied, and a second film 25 which, as shown in FIG. 11, is applied to the opposite side of the napkins. The sleeve formed by the two plastic films is welded together longitudinally on either side of the napkins and is welded between adjoining napkins in the package by means of two mutually spaced weld joints 26,27 with an intermediate perforation 28. The sanitary napkins will thus be enclosed in one-piece parcels. In each separate parcel there is a perforation 29 made in the second plastic film through which the sanitary napkin can be taken out. The package unit according to FIG. 11 is folded or rolled together into one or more piles of napkins. The folded or rolled-up unit can be kept together with the aid of hot melt spots for example, in a manner similar to that described with reference to FIG. 9. One or more one-piece parcels, which completely enclose each individual napkin, can be separated from the package unit. After taking out one sanitary napkin of a one-piece parcel, the empty parcel can be kept to serve as a refuse bag for the used napkin.

Figure 12:
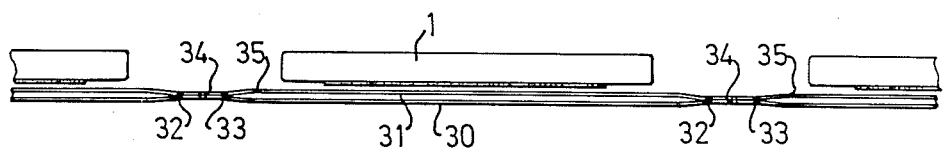

FIG. 12 illustrates a further embodiment of a package according to the invention including two elongate plastic films 30,31 welded together along their longitudinal edges and at uniform mutual intervals transversely. The transverse joints are made as two adjoining welding seams 32,33 with intermediate perforations 34. These perforations 34 serve to delimit individual one-piece parcels for sanitary napkins. In one of the plastic films there is made for each parcel a perforation 35 intended to serve as a parcel opening. The path formed by the two plastic films is treated on one side with release agent. A sanitary napkin 1 is intended to be placed centrally on each parcel with its adhesive strips in contact with the release agent treated side of the path. As is the case in the embodiments described above, a package is formed with the sanitary napkins stacked on top of one another by folding or rolling up the path carrying the napkins. Prior to folding or rolling up, the path is provided with hot melt spots, as was the case in the embodiment illustrated in FIG. 9 for keeping the package unit together. During the packing operation, the parcels under each separate sanitary napkin will serve as release paper, and after disposal of the used napkin or pad as a refuse bag for it.

The invention is not restricted to the exemplary embodiments described above; a plurality of modifications are conceivable within the scope of the following claims. It is not necessary for example, as described with reference to FIGS. 1-6, to arrange perforations in the longitudinal direction of the plastic film outside both ends of the sanitary napkin. As a matter of fact, it has appeared that in welding seams where a surface treated with release agent is in direct contact with a non-treated surface, the welding seam will be strong enough but also easily torn off. If, on the other hand, a surface treated with release agent is in direct contact with another similarly treated surface, the welding seam will be much to weak. If two non-treated plastic film surfaces are applied in direct contact with one another and welded, however, the welding seam will be too strong to be torn open manually.

Thus, instead of perforating the plastic sheet it can be rolled up so that portions treated with release agent are brought in direct contact with non-treated portions for subsequent welding. This is achieved, except for the initial folding, by rolling up as illustrated in FIGS. 3 and 4. The perforations 10 and 11 are thus superfluous.

In the embodiment described with reference to FIG. 11 the perforations 29, i.e. the package opening, can be replaced by another type of opening, suitably in the form of two overlapping path portions of the plastic film 25, thereby achieving a resealable one-piece parcel to be utilized for the disposal of a sanitary napkin after use, for example.

In the embodiment described according to FIG. 12, the separate but interconnected parcels can have a length and width primarily twice that of the sanitary napkin, i.e. applying two napkins on each parcel. In this way the size of the parcel will be large enough to enclose a used napkin even in its folded state.

In the above-described exemplary embodiments, the package material mentioned is plastic film. The package film can of course be replaced by another material such as paper, for example.

We claim:

1. Package for menstrual protectors such as sanitary napkins and pads or panty protectors having, on their side facing away from the body of the user, areas coated with pressure-sensitive adhesive intended, when using the napkin, for sticking to the underwear of the user to keep the napkin in place, characterized in that a plurality of sanitary napkins are detachably disposed and mutually spaced in one or more rows with their adhering side placed in contact with a film, preferably of paper or plastic, the film with the napkins applied thereon being folded so that the napkins are laid on top of one another to form one or more piles, the film in its folded condition enclosing the sanitary napkins applied thereon, the film extending laterally outside the sanitary napkins, after folding of the film with the napkins placed thereon, being sealed there by welding, gluing or the like.

2. Package as claimed in claim 1, characterized in that the film on the inside of the joint line but laterally outside the sanitary napkins, and on either side thereof, is provided with perforations along which the package can be torn open.

3. Package as claimed in claim 1, characterized in that the film is provided with a perforation extending across it in the areas between adjoining sanitary napkins.

4. Package as claimed in claim 1, characterized in that the side of the flim facing the adhesive areas of the sanitary napkins is embossed or provided with release agent such as silicon for reducing the adhesive effect between the film and the napkins.

5. Package as claimed in claim 1, characterized in that the package includes a second film applied on the opposite side of the napkins which are mutually spaced in one or more rows on the first film, that the two films are welded together around each napkin, there being arranged between adjacent napkins in the package two mutually spaced welding seams with an intermediate perforation, and that the second film, on either side of the one-piece parcels formed by welding, is provided with an opening or perforation for enabling the napkins to be taken out of each one-piece parcel.

6. Package as claimed in claim 1, characterized in that the package includes a second film which is in direct contact with the first film and is welded together with it around each napkin, there being arranged between adjoining napkins in the package two mutually spaced welding seams with an intermediate perforation, and that one film, on either side of the one-piece parcels formed by welding, is provided with an opening or perforation.

7. Package for menstrual protectors such as sanitary napkins and pads or panty protectors having, on their side facing away form the body of the user, areas coated with pressure-sensitive adhesive intended, when using the napkin, for sticking to the underwear of the user to keep the napkin in place, characterized in that a plurality of sanitary napkins are detachably disposed and mutually spaced in one or more rows with their adhering side placed in contact with a film, preferably of paper or plastic, the film with the napkins applied thereon being rolled up so that the napkins are laid on top of one another to form one or more piles, the film in its rolled-up condition enclosing the sanitary napkins applied thereon, the film extending laterally outside the sanitary napkins, after rolling up of the film with the napkins placed thereon, being sealed there by welding, gluing or the like.

8. Package as claimed in claim 7, characterized in that the film on the inside of the joint line but laterally outside the sanitary napkins, and on either side thereof, is provided with perforations along which the package can be torn open.

9. Package as claimed in claim 7, characterized in that the film is provided with a perforation extending across it in the areas between adjoining sanitary napkins.

10. Package as claimed in claim 7, characterized in that the side of the film facing the adhesive areas of the sanitary napkins is embossed or provided with release agent such as silicone for reducing the adhesive effect between the film and the napkins.

11. Package as claimed in claim 10, wherein the film is sealed together laterally outside the napkins by means of welding seams, characterized in that the film with the sanitary napkins placed thereon is rolled up from one end, one pile length or width at the time, to form a pile of napkins in which one path portion treated with release agent and measuring one pile length or width is in contact with a path portion of the non-treated film surface having the same size, whereby the welding seams outside the napkins will be sufficiently strong but still easily openable.

12. Package as claimed in claim 7, characterized in that the package inludes a second film applied on the opposite side of the napkins which are mutually spaced in one or more rows on the first film, that the two films are welded together around each napkin, there being arranged between adjacent napkins in the package two mutually spaced welding seams with an intermediate perforation, and that the second film, on either side of the one-piece parcels formed by welding, is provided with an opening or perforation for enabling the napkins to be taken out of each one-piece parcel.

13. Package as claimed in claim 7, characterized in that the package includes a second film which is in direct contact with the first film and is welded together with it around each napkin, there being arranged between adjoining napkins in the package two mutually spaced welding seams with an intermediate perforation, and that one film, on either side of the one-piece parcels formed by welding, is provided with an opening or perforation.

14. Package for menstrual protectors such as sanitary napkins and pads or panty protectors having, on their side facing away form the body of the user, areas coated with pressure-sensitive adhesive intended, when using the napkin, for sticking to the underwear of the user to keep the napkin in place, characterized in that a plurality of sanitary napkins are detachably disposed and mutually spaced in one or more rows with their adhering side placed in contact with a film, preferably of paper or plastic, the film with the napkins applied thereon being folded and rolled up so that the napkins are laid on top of one another to form one or more piles, the film in its folded and rolled-up condition enclosing the sanitary napkins applied thereon, the film extending laterally outside the sanitary napkins, after folding and rolling up of the film with the napkins placed thereon, being sealed there by welding, gluing or the like.

15. Package as claimed in claim 14, characterized in that the film on the inside of the joint line but laterally outside the sanitary napkins, and on either side thereof, is provided with perforations along which the package can be torn open.

16. Package as claimed in claim 14, characterized in that the film is provided with a perforation extending across it in the areas between adjoining sanitary napkins.

17. Package as claimed in claim 14, characterized in that the side of the film facing the adhesive areas of the sanitary napkins is embossed or provided with release agent such as silicone for reducing the adhesive effect between the film and the napkins.

18. Package as claimed in claim 14, characterized in that the package includes a second film applied on the opposite side of the napkins which are mutually spaced in one or more rows on the first film, that the two films are welded together around each napkin, there being arranged between adjacent napkins in the package two mutually spaced welding seams with an intermediate perforation, and that the second film, on either side of the one-piece parcels formed by welding, is provided with an opening or perforation for enabling the napkins to be taken out of each one-piece parcel.

19. Package as claimed in claim 14, characterized in that the package includes a second film which is in direct contact with the first film and is welded together with it around each napkin, there being arranged between adjoining napkins in the package two mutually spaced welding seams with an intermediate perforation, and that one film, on either side of the one-piece parcels formed by welding, is provided with an opening or perforation.

* * * * *